United States Patent
Eckhardt et al.

(10) Patent No.: US 7,775,126 B2
(45) Date of Patent: Aug. 17, 2010

(54) FLUID FLOW MONITOR

(75) Inventors: Todd Eckhardt, Westerville, OH (US); Richard Wade, Worthington, OH (US); Ryan Jones, Dublin, OH (US)

(73) Assignee: Honeywell International Inc., Morristown, NJ (US)

( * ) Notice: Subject to any disclaimer, the term of this patent is extended or adjusted under 35 U.S.C. 154(b) by 121 days.

(21) Appl. No.: 12/256,181

(22) Filed: Oct. 22, 2008

(65) Prior Publication Data

US 2010/0100052 A1    Apr. 22, 2010

(51) Int. Cl.
*G01F 1/37* (2006.01)
*A61M 31/00* (2006.01)

(52) U.S. Cl. .............. 73/861.52; 73/861.47; 604/93.01; 604/131; 604/246

(58) Field of Classification Search ........................ None
See application file for complete search history.

(56) References Cited

U.S. PATENT DOCUMENTS

| | | | |
|---|---|---|---|
| 4,395,915 A | 8/1983 | Singh | |
| 4,528,855 A | 7/1985 | Singh | |
| 5,656,785 A | 8/1997 | Trainor et al. | 73/862.046 |
| 6,229,190 B1 | 5/2001 | Bryzek et al. | |
| 6,612,179 B1 | 9/2003 | Kurtz | |
| 7,296,479 B2 | 11/2007 | Hogeland | 73/800 |
| 2005/0229720 A1 | 10/2005 | Hanazawa et al. | 73/862.042 |
| 2006/0000265 A1 | 1/2006 | Parker et al. | |
| 2008/0114256 A1 | 5/2008 | Zhang et al. | 600/488 |
| 2008/0127743 A1 | 6/2008 | Schadler et al. | 73/826 |

OTHER PUBLICATIONS

Force Sensors, FSG and FSL Series; Sensing and Control; Honeywell International Inc.
Pressure Sensors FSO1/FS03 Force Sensors; Sensing and Control; Honeywell International Inc.
Kremer et al., "Signal Conditioning Circuits for Sensors Frame ASICs or Modular Signal Conditioning," 8 pages, Analog Microelectronics, Aug. 2000.

*Primary Examiner*—Harshad Patel

(57) ABSTRACT

A differential force sensor method and apparatus for automatically monitoring manual injections through an intravenous line. The differential force sensor includes two piezoresistive sense die that are packaged in close proximity utilizing a number of packaging processes. The two piezoresistive sense die can be utilized to measure forces exerted on a diaphragm on either side of an orifice. The piezoresistive sense die can be packaged in close proximity to make intimate contact with the diaphragms on either side of the orifice. The differential force sensor further includes two plungers that make intimate contact with the diaphragm and transfer the force into the piezo-resistive sense dies. Additionally, one or more ASICs and microcontrollers can be utilized to provide thermal calibration and differential calculation.

19 Claims, 7 Drawing Sheets

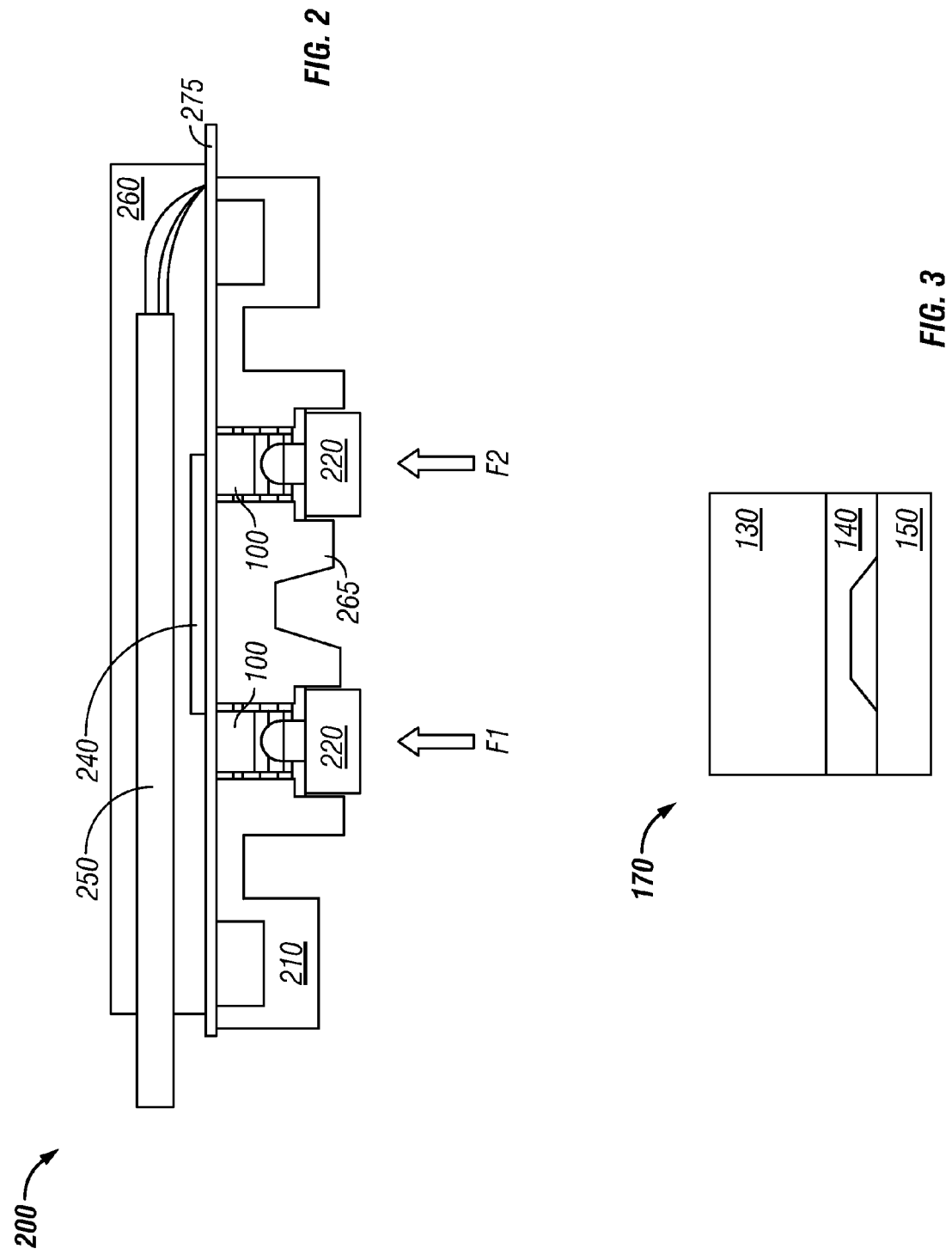

FLUID FLOW MONITOR

TECHNICAL FIELD

Embodiments are generally related to sensor methods and systems. Embodiments are also related to differential force sensors. Embodiments are additionally related to differential force sensors utilized in the context of monitoring manual patient injections through an intravenous line.

BACKGROUND OF THE INVENTION

In the medical field, it is common for intravenous (IV) medications such as, for example, antibiotics, antiviral, antiemetic, chemotherapy, and so forth, to be administered intermittently with a frequency as often as multiple times per day. Depending on the frequency of administration, the patient is either repeatedly connected to and disconnected from an IV line or is continuously connected to an IV line between administrations. In either case, the intermittent medications are generally administered by trained personnel utilizing predefined procedures that often include a series of manual steps and a large number of disposable supplies. Each manual step in such procedures increases the risks associated with multiple manipulations and entry of IV sites.

Patient injections through IV lines can be currently recorded manually. The nurse administering the medication must follow strict guidelines regarding the quantity of medication to be administered and potentially the rate at which the medication should be administered. Also, regular monitoring of infusion sites assists in reducing the severity of adverse effects when infiltration and extravasations occur. Hence, an automated method for monitoring manual injections through an IV line is desired.

Based on the foregoing, it is believed that a need exists for an improved differential force sensor for automatically monitoring manual injections through an IV line. Also, a need exits for a small-sized and lightweight differential force sensor that is capable of being utilized in close proximity to the injection point in a patient's body to reduce patient discomfort.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensor method and apparatus.

It is another aspect of the present invention to provide for an improved differential force sensor apparatus capable of automatically monitoring manual injections through an IV line.

The aforementioned aspects and other objectives and advantages can now be achieved as described herein. A differential force sensor apparatus and method for automatically monitoring manual injections through an intravenous line is disclosed. The differential force sensor includes two piezoresistive sense die packaged in close proximity utilizing any one of a number of packaging processes. The two piezoresistive sense die can be utilized to measure force exerted on a diaphragm on either side of the orifice. The piezoresistive sense die can be packaged in close proximity to make intimate contact with a diaphragm(s) located on either side of the orifice. The differential force sensor further includes one or more plungers that make intimate contact with the diaphragm and transfer the force to the piezoresistive sense die. Additionally, one or more ASIC components and microcontrollers can be utilized to provide thermal calibration and differential calculation.

In one embodiment, each piezoresistive sense die can be packaged utilizing a conductive seal stack, which includes a conductive seal and an environmental seal. The conductive seal stacks can be placed on a PCB (Printed Circuit Board) and held captive by a single piece of plastic housing. The single plastic housing includes, for example, two plungers that make intimate contact with the flow diaphragm and transfer the force into the piezoresistive sense die.

In a second embodiment, each piezoresistive sense die associated with the differential force sensor can be glued to a PCB. A housing can be positioned over the piezoresistive sense die, whereby a gel is then dispensed and cured into an orifice formed above the piezoresistive sense die in order to make intimate contact with the topside of the sense die. The diaphragm and the plunger can be placed on top of the gel. The force from an external diaphragm can be transmitted through the plunger and into the gel and finally into the piezoresistive sense die.

In a third embodiment, each piezoresistive sense die associated with the differential force sensor can be glued to a carrier. The gel can be dispensed into an orifice in the carrier which allows the gel to make intimate contact with the backside (e.g., etched side) of the sense die. A carrier assembly can be glued to a PCB so that the sense die is then electrically connected. The diaphragm can be placed over the cured gel and a cover is located over the system to maintain the diaphragm in place and provide an environmental seal. The signal compensation for the differential force sensor can be performed in two ASICS (one for each piezoresistive sense die) and the microcontroller can be utilized to communicate with external electronics. Note that any combination of the above embodiments may also be used, such as, for example, a sense die glued to a PCB, wherein as a ball bearing makes intimate contact with the sense die diaphragm, the force is transmitted to the ball bearing, and so forth.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

FIG. 2 illustrates a cross-sectional view of a differential force sensor with two piezoresistive sense die, each packaged by means of the conductive seal stack, in accordance with a first embodiment;

FIG. 3 illustrates an exploded view of the conductive seal stack, in accordance with a first embodiment;

DETAILED DESCRIPTION

The particular values and configurations discussed in these non-limiting examples can be varied and are cited merely to illustrate at least one embodiment and are not intended to limit the scope thereof.

Figure 1:
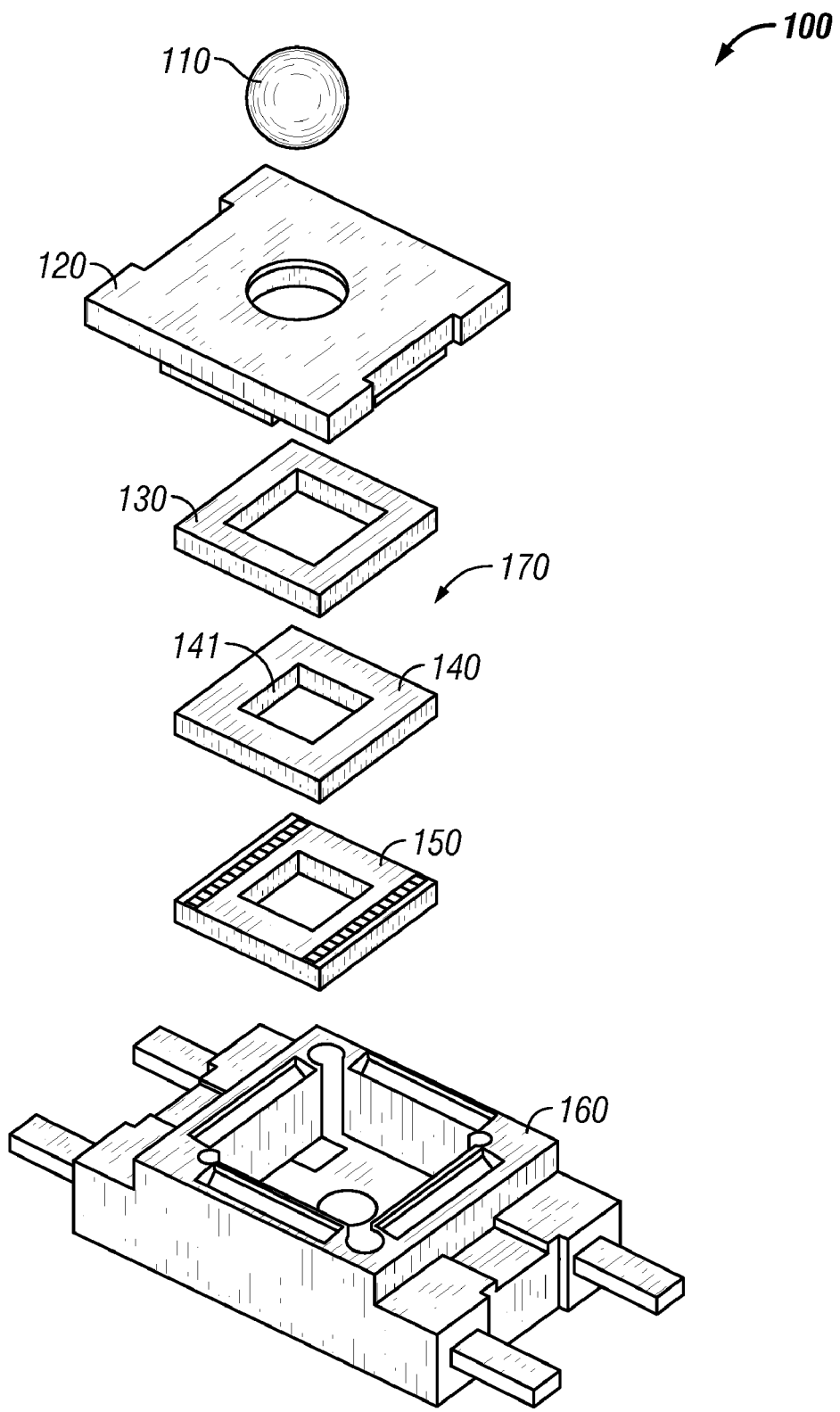
FIG. 1 illustrates an exploded view of a force sensor with piezo-resistive sense die packaged by means of conductive seal stack, in accordance with a first embodiment.

FIG. 1 illustrates an exploded view of a force sensor 100 having a piezoresistive sense die 140 packaged utilizing a conductive seal stack 170, in accordance with a preferred embodiment. As illustrated in FIG. 1, the conductive seal stack 170 generally includes a conductive seal 150 and an environmental seal 130. The conductive seal 150 and the piezoresistive sense die 140 can be inserted into a housing 160 with the environmental seal 130 inserted last over the sense die 140. The active side of the die 140 can be faced down into the housing 160. A cover 120 can be assembled to the housing 160 and can be pressed into place. A ball bearing 110 can be assembled to the force sensor 100 and can be pressed into the cover 120. The sense die 140 can include a diaphragm 141 and multiple electrically conductive bond pads (not shown) therein.

The diaphragm 141 can be utilized for absorbing the pressure or force applied. The diaphragm 141 can be made of thin silicon materials in order to measure even very minute pressure. The electrically conductive bond pads of the sense die 140 can be electrically connected to the diaphragm 141 in order to output electrical signals. Furthermore, the diaphragm 141 can be incorporated with piezoresistive elements (not shown) that convert the deformation of the diaphragm 141 due to the applied force into electrical signals utilizing well-known piezoresistive principles in order to compute the pressure in the media. The bond pads of the sense die 140 can be integrated on the piezoresistive elements. The sense die 140 can be electrically connected with the conductive elastomeric seal 150 in order to electrically connect several external electrical terminals or molded leads to the sense die 140. The housing 160 can include a set of lugs that can be utilized to snap the housing 160 and the cover 120 together. Such force sensor 100 can improve the accuracy of the sensing output signal.

FIG. 2 illustrates a cross-sectional view of a differential force sensor 200 with two force sensors 100 each packaged by means of a conductive seal stack 170, in accordance with a first embodiment. Note that in FIGS. 1-9, identical or similar parts or elements are generally indicated by identical reference numerals. The two force sensors 100 can be packaged by means of a conductive seal stack 170, which includes the conductive seal 150 and the environmental seal 130, as depicted in FIG. 1. The force sensors 100 can be placed on a PCB (Printed Circuit Board) 275 and held captive by a single piece of plastic housing 265. The single plastic housing 265 includes two plungers 220 that make intimate contact with a flow diaphragm (not shown) and transfer the force into the piezoresistive sense die 140 associated with the force sensors 100. The differential force sensors 100 can be covered with a bottom cover 210 and a top cover 260.

Figure 9:
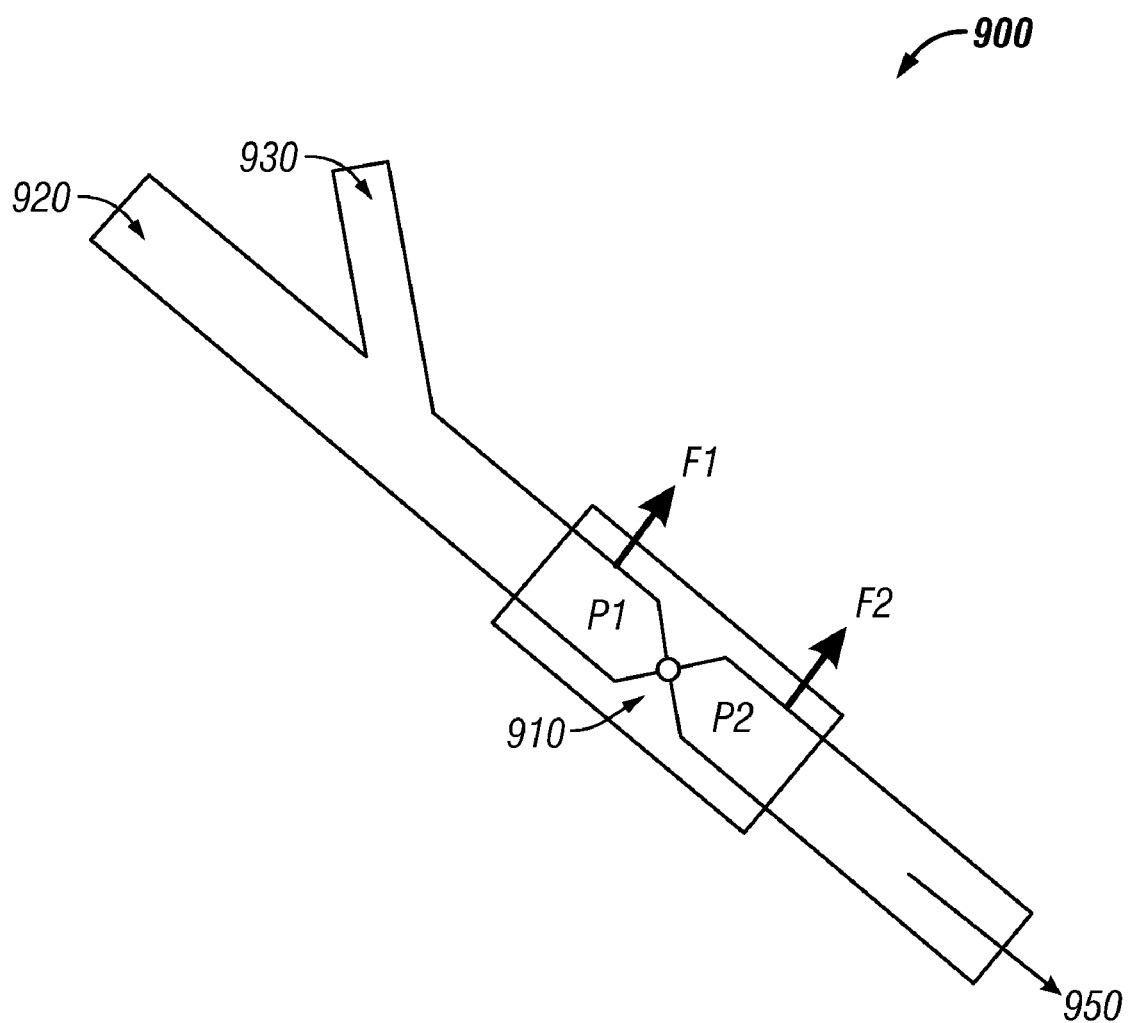
FIG. 9 illustrates a schematic diagram of an intravenous fluid delivery system utilizing differential force sensor on either side of an orifice for monitoring manual injections, which can be implemented in accordance with a preferred embodiment.

FIG. 3 illustrates an exploded view of the conductive seal stack 170. The conductive seal stack 170 comprises the conductive seal 150, the piezoresistive sense die 140 and the environmental seal 130. The two-force sensors 100 can be utilized to measure forces exerted on the diaphragm on either side of an orifice 910, as shown in FIG. 9. The two-force sensors 100 can be packaged in close proximity to make intimate contact with the diaphragms on either side of the orifice 910. The forces F1 and F2 on either side of the orifice 910 can be measured. Additionally, one or more ASICs (not shown) can be utilized to provide linearization and thermal compensation through calibration and differential calculation. A microcontroller 240 can be utilized to provide the differential calculation or flow rate calculation and communicate with external electronics through an USB cable 250.

Figure 4:
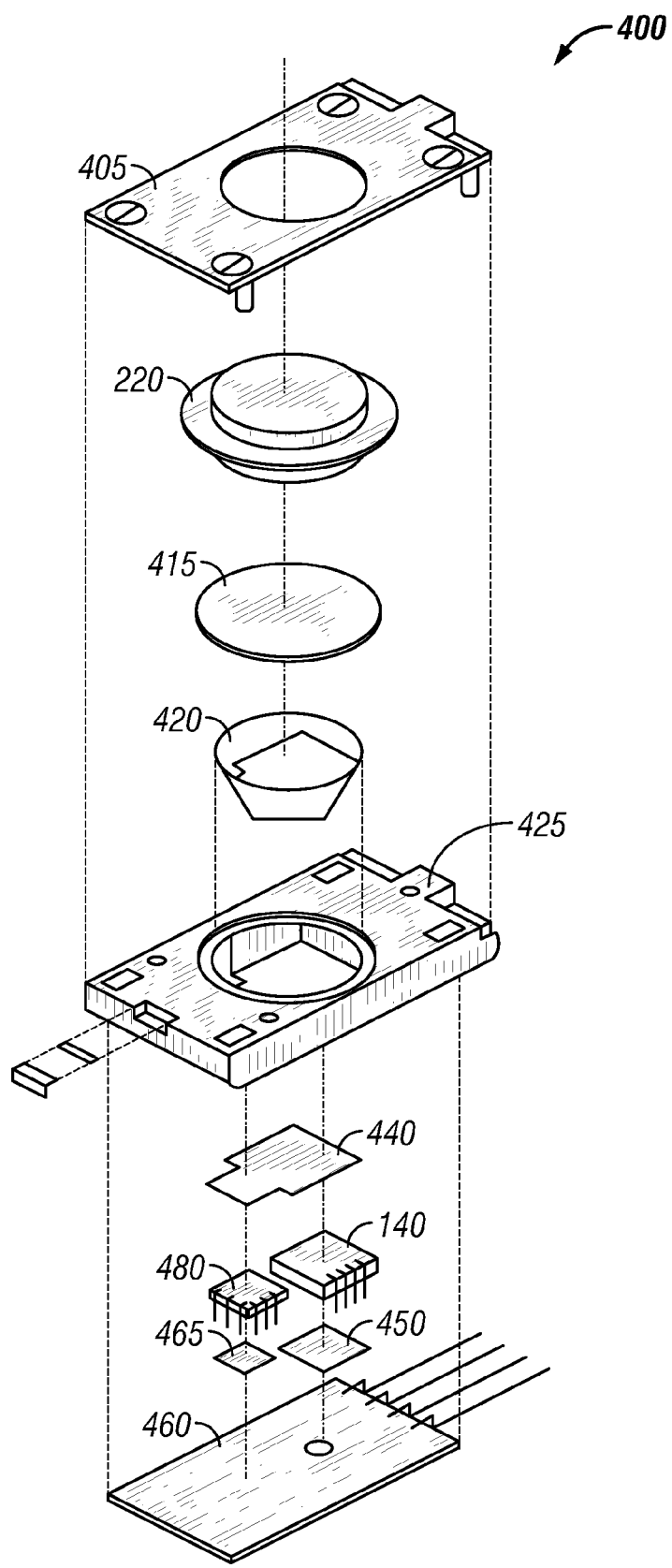
FIG. 4 illustrates an exploded view of a force sensor with piezo-resistive sense die glued to a printed circuit board (PCB), in accordance with a second embodiment.

FIG. 4 illustrates an exploded view of a force sensor 400 with piezoresistive sense die 140 glued to a printed circuit board (PCB) 460, in accordance with a second embodiment. The piezoresistive sense die 140 can be glued to the PCB 460 by means of glue 450. The differential force sensor 400 features an integrated circuit sensor element in the form of piezoresistive sense die 140 and the PCB 460 in a small plastic housing 425. Such a sensor 400 with extremely small size enables the use of multiple sensors in limited available space. Such package also provides excellent corrosion resistance and isolation to external package stress. The differential force sensor 400 comprises a dual amplifier 480 bonded to the PCB 460 utilizing an epoxy 465. A cover 405 can be placed over the sensor 400 in order to provide an environmental seal. The molded housing 425 can be positioned over the sense die 140 utilizing an epoxy 440, whereby a gel 420 can be dispensed and cured into the orifice 910 above the sense die 140 so it makes intimate contact with the topside of the sense die 140. A Kapton diaphragm 415 and the plunger 220 can be placed on top of the gel 420.

Figure 5:
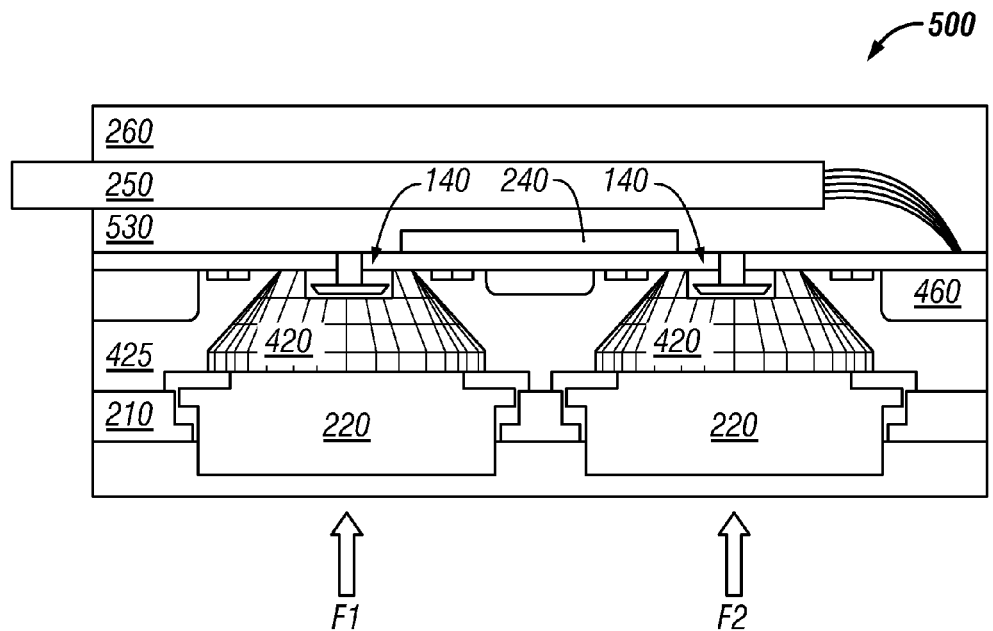
FIG. 5 illustrates a cross sectional view of a differential force sensor with two piezoresistive sense die, each glued to the PCB, in accordance with a second embodiment.

FIG. 5 illustrates a cross-sectional view of a differential force sensor 500 with two-piezoresistive sense die 140 each glued to the PCB 460, in accordance with a second embodiment. The two force sensors 400 comprising the piezo-resistive sense die 140 that are packaged in close proximity can be glued to the PCB 460. The molded housing 425 can be positioned over the sense die 140, whereby the gel 420 can be dispensed and cured into the orifice 910 above the sense die 140 so it makes intimate contact with the topside of the sense die 140.

The diaphragm 415 and the plunger 220 can be placed on top of the gel 420. The two-piezoresistive sense die 140 can be utilized to measure forces exerted on the diaphragm 415 on either side of the orifice 910. The forces F1 and F2 from the diaphragm 415 can be transmitted through the plungers 220 and into the gel 420 and finally into the piezo-resistive sense die 140. The signal compensation for the piezoresistive sense die 140 can be completed through ASICs 530. The microcontroller 240 can be utilized to communicate with external electronics through the USB cable 250. The differential force sensor 500 can be covered with a bottom cover 210 and a top cover 260.

Figure 6:
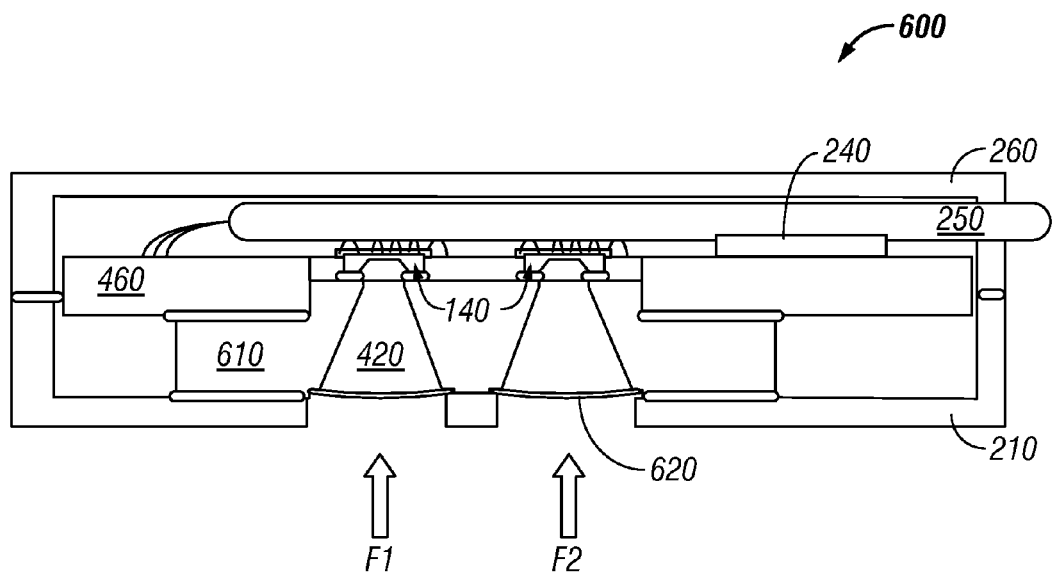
FIG. 6 illustrates a cross-sectional view of the differential force sensor with two piezoresistive sense die, each glued to a carrier, in accordance with a third embodiment.

FIG. 6 illustrates a cross-sectional view of a differential force sensor 600 with two piezoresistive sense die 140 each glued to a carrier 610, which can be implemented in accordance with a third embodiment. Again as reminder, in FIGS. 1-9 identical or similar parts or elements are generally indicated by identical reference numerals. The piezo-resistive sense die 140 can be glued to the carrier 610 and the gel 420 can be dispensed into the orifice 910 in the carrier 610 which allows the gel 420 to make intimate contact with the back side (etched side) of the sense die 140. The carrier assembly 610 can be glued to the PCB 460 so that the sense die 140 can be electrically connected.

The diaphragm 415 can be placed over the cured gel 420 and a protective cover 620 can be placed over the gel 420 to hold the diaphragm 415 in place and provide an environmental seal. The differential force sensor 600 further comprises a top housing 260 that contains strain relief and a bottom housing 210 that holds the protective cover 620 in place. The signal compensation for the piezoresistive sense die 140 can be completed through two ASICs (not shown) and the microcontroller 240 can be utilized to communicate with external electronics through the USB cable 250.

Figure 7:
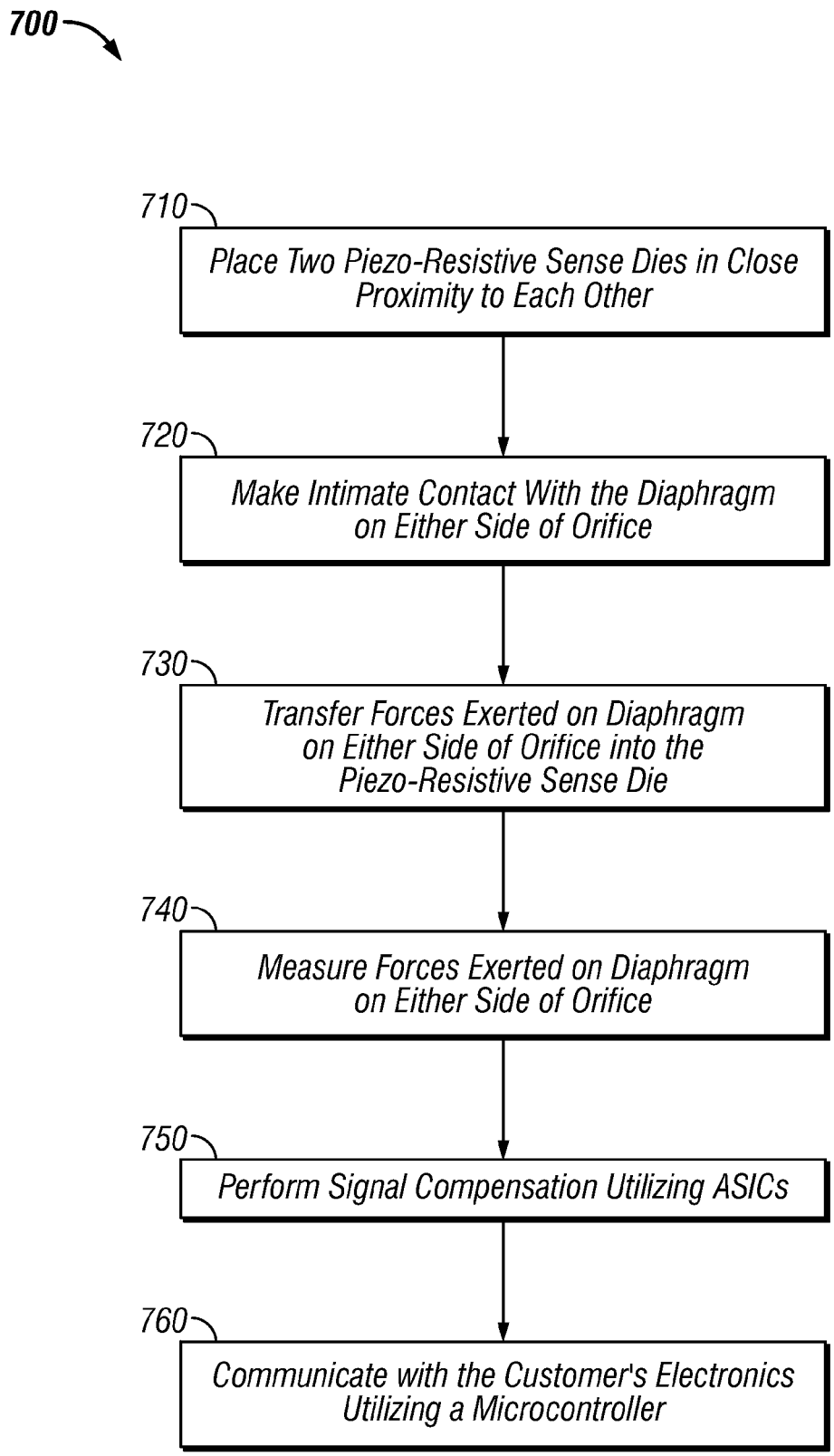
FIG. 7 illustrates a high level flow chart of operations illustrating logical operational steps of a method for automatically monitoring manual injections through an intravenous line utilizing the differential force sensor, in accordance with a preferred embodiment.

FIG. 7 illustrates a high level flow chart of operations illustrating logical operational steps of a method 700 for automatically monitoring manual injections through an intravenous line 920 utilizing the differential force sensor 200, 500 and 600, in accordance with a preferred embodiment. The two-piezoresistive sense die 140 can be packaged in close proximity utilizing a number of packaging processes, as depicted at block 710. An intimate contact can be made with the diaphragm on either side of the orifice 910, as depicted at block 720. Thereafter, forces F1 and F2 exerted on the diaphragm on either side of the orifice 910 can be transferred into the piezoresistive sense die 140, as depicted at block 730. The forces F1 and F2 exerted on diaphragm on either side of the orifice 910 can be measured, as depicted at block 740. Next, signal compensation can be performed in the ASICs, as depicted at block 750.

The microcontroller 240 can be utilized to calculate the differential force and associated flow and communicate with external electronics for further communication, as depicted at block 760. Such an automated method 700 monitors manual injections through an IV line utilizing a non-contact differential force measurement on either side of the orifice 910. The output of the differential force sensor 200, 500 and 600 can be the individual force measurements in the form of an electrical signal (i.e., digital or analog) and potentially a differential signal (i.e., the difference between the two sense elements). Additionally, the small size and lightweight of the sensor 200, 500 and 600 reduce patient discomfort possible through close proximity of the device to the injection point in the patient's body.

Figure 8:
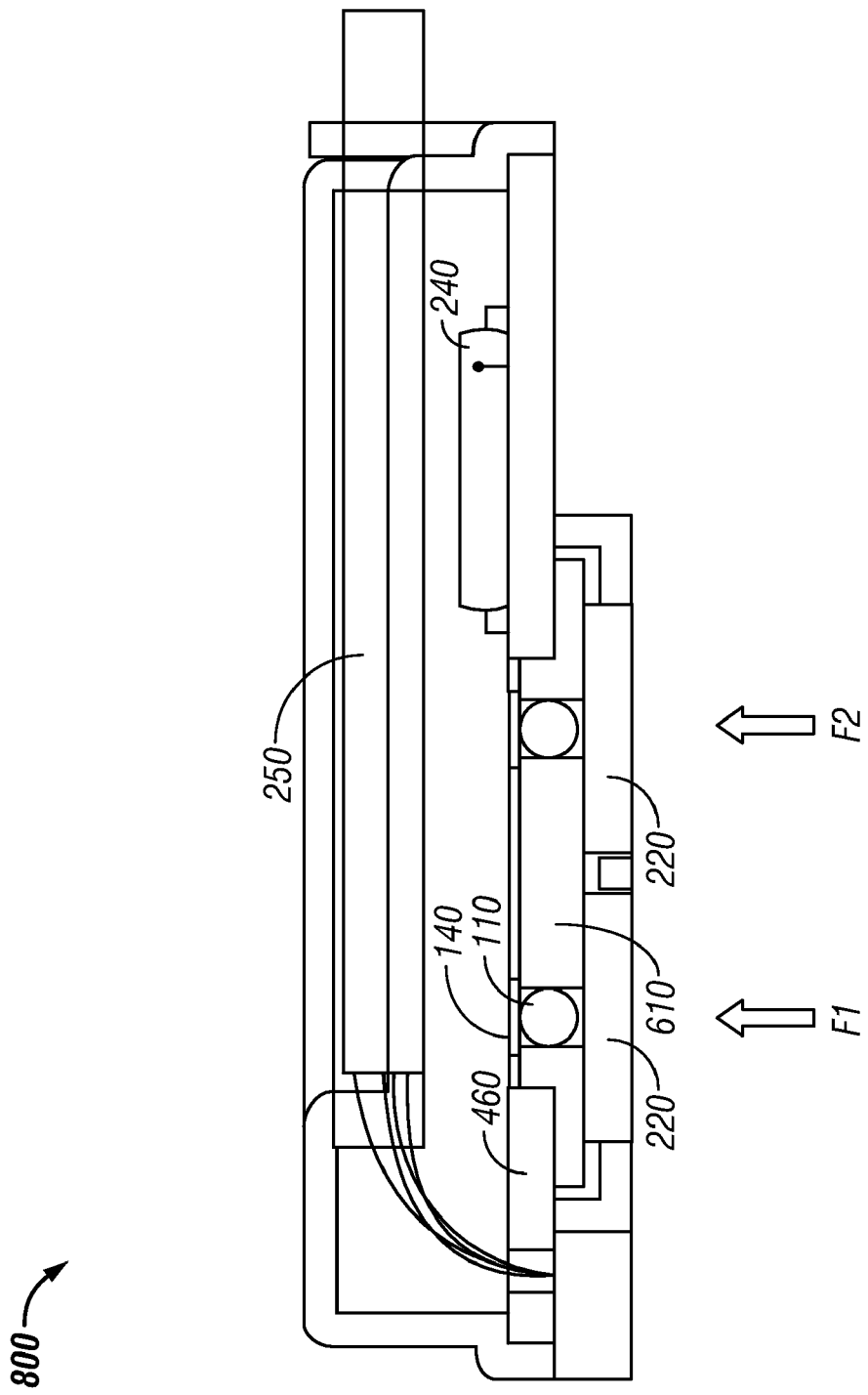
FIG. 8 illustrates a cross-sectional view of a differential force sensor glued to the carrier with mechanical contact from a ball bearing and a plunger, in accordance with a preferred embodiment.

FIG. 8 illustrates a cross-sectional view of a differential force sensor 800 glued to the carrier 610 with mechanical contact from the ball bearing 110 and the plunger 220, in accordance with a preferred embodiment. The piezo-resistive sense die 140 can be glued to the carrier 610. The force F1 and F2 can be transferred to the sense die 140 through the plunger 220 and the ball bearing 110. Note that the sense die 140 can also be attached to the PCB 460 with mechanical contact from the ball bearing 110 and/or the plunger 220. The signal compensation can be performed in two ASICs and a microcontroller 240 can be utilized to communicate with external electronics through the USB cable 250. Note that the embodiments discussed herein should not be construed in any limited sense. It can be appreciated, of course, that other types of combination of the above embodiments may also be utilized such as, for example, the sense die glued to the PCB, wherein as a ball bearing makes intimate contact with the sense die diaphragm, the force is transmitted to the ball bearing, and so forth. However, it will be apparent to those skilled in the art that other combinations can be utilized as desired without departing from the scope of the invention.

FIG. 9 illustrates a schematic diagram of an intravenous fluid delivery system 900 utilizing differential force sensors such as sensor 200, 500, 600 and 800 on either side of the orifice 910 for monitoring manual injections, which can be implemented in accordance with a preferred embodiment. The intravenous fluid delivery system 900 includes an intravenous tube 920 and an injection point 930 for delivering medications to a patient, as illustrated by arrow 950. The differential force sensor such as sensor 200, 500, 600 and 800, which includes piezoresistive sense die 140, can be placed on either side of the orifice 910 for measuring differential force on either side of the orifice 910. The piezoresistive sense die 140 can be utilized to measure forces F1 and F2 exerted on the diaphragm 415 on either side of the orifice 910. The piezoresistive sense die 140 can be packaged in close proximity to make intimate contact with the diaphragm(s) 415 located on either side of the orifice 910.

The intravenous medications such as, for example, antibiotics, antivirals, antiemetics, chemotherapy, and biotechnology drugs can be administrated intermittently with a frequency through the injection point 930. Depending on the frequency of administration, the patient is either repeatedly connected to and disconnected from the intravenous line or is continuously connected to the intravenous line between administrations. The differential force sensor such as sensor 200, 500, 600 and 800 can be mounted very close to the point of entry into the patient's body. Such differential force sensor such as sensor 200, 500, 600 and 800 is capable of automatically monitoring manual injections through the intravenous line 920. The output of the sensor can be the individual force measurements in the form of an electrical signal (either digital or analog) and potentially a differential signal (the difference between the two sense elements). Such small size and lightweight differential force sensor for monitoring manual injections through the intravenous line 920 reduce patient discomfort.

Such differential force sensor 200, 500, 600 and 800 is a high-performance transducer specifically designed to address the needs of medical and specialized OEM (original equipment manufacturer) applications. The differential force sensor 200, 500, 600, and 800 can be specified to operate with either a constant current or voltage supply. Each force sensor 200, 500, 600 and 800 employs a solid-state piezo-resistive pressure transducer mounted in a plastic package. Such an approach provides a reliable solution for applications where force can be applied by a flexible membrane to the sensor, such as that found in infusion pumps. The differential force also provides access to important safety features in critical care medical instrumentation such as occlusion pressure or infiltration detection. The pressure data can provide medical personnel with useful diagnostic information regarding the condition of the patient's circulatory system. The differential force sensor can also be utilized with other medical dispensing devices, such as syringe pumps, to improve safety and accuracy.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A method for monitoring fluid flow through a fluid line having an orifice along the length of the fluid line, comprising:

providing a package that includes a plurality of piezoresistive sense die in close proximity to one another, wherein a first one of said plurality of piezoresistive sense die is situated adjacent to a first flow diaphragm situated on a first side of the orifice, and a second one of said plurality of piezoresistive sense die is situated adjacent to a second flow diaphragm positioned on a second side of the orifice;

transferring a force from said first flow diaphragm to said first piezoresistive sense die through a first plunger, and transferring a force from said second flow diaphragm to said second piezoresistive sense die through a second plunger; and performing a signal compensation utilizing at least one electronic device associated with said plurality of piezoresistive sense die to thereby provide a thermal calibration and a differential calculation, wherein said at least one electronic device communicates electronically with external electronics to automatically monitor fluid flow through the fluid line.

2. The method of claim 1 wherein the first plunger includes a first ball bearing and the second plunger includes a second ball bearing.

3. The method of claim 1 further comprising configuring said plurality of piezoresistive sense die to include two piezoresistive sense die.

4. The method of claim 1 wherein providing the package that includes said plurality of piezoresistive sense die in close proximity to one another further comprises:

placing each of said plurality of piezoresistive sense die between a conductive seal stack; and locating said conductive seal stack on a PCB held captive by a plastic housing.

5. The method of claim 4 wherein said conductive seal stack comprises an environmental seal and a conductive seal.

6. The method of claim 1 wherein providing the package that includes said plurality of piezoresistive sense die in close proximity to one another, further comprises:

gluing each piezoresistive sense die among said plurality of piezoresistive sense die to a PCB;

positioning a housing over said plurality of piezoresistive sense die; and dispensing and curing a gel into an orifice formed above said plurality of piezoresistive sense die in order to make intimate contact with a top side of at least one piezoresistive sense die among said plurality of piezoresistive sense die.

7. The method of claim 6 wherein said first and second plungers and said first and second flow diaphragms are positioned above said gel such that a force from said first and second flow diaphragms is transmitted through said first and second plungers and into said gel and finally into said first and second piezoresistive sense die, respectively.

8. The method of claim 1 wherein providing the package that includes said plurality of piezoresistive sense die in close proximity to one another, further comprises:

gluing to a carrier, each piezoresistive sense die among said plurality of piezoresistive sense die;

dispensing a gel into an orifice in said carrier in order to allow said gel to make intimate contact with an etched side of the first one of said plurality of piezoresistive sense die;

placing said first flow diaphragm over said gel; and locating a cover over said carrier to maintain said first flow diaphragm in place and to provide an environmental seal.

9. The method of claim 8 further comprising gluing said carrier to a PCB so that said at least two of the plurality of piezoresistive sense die are electrically connected to one another.

10. A method for monitoring fluid flow in a fluid line having an orifice along the length of the fluid line, comprising:

providing a package that includes a plurality of piezoresistive sense die in close proximity to one another, wherein a first one of said plurality of piezoresistive sense die is situated adjacent to a first flow diaphragm situated on a first side of the orifice, and a second one of said plurality of piezoresistive sense die is situated adjacent to a second flow diaphragm positioned on a second side of the orifice;

transferring a force from said first flow diaphragm to said first piezoresistive sense die through a first plunger, and transferring a force from said second flow diaphragm to said second piezoresistive sense die through a second plunger; and performing a signal compensation utilizing at least one ASIC component and a microcontroller associated with said plurality of piezoresistive sense die to thereby provide a thermal calibration and a differential calculation, wherein said microcontroller communicates electronically with external electronics for automatically monitoring fluid flow through the fluid line.

11. The method of claim 10 wherein providing the package that includes said plurality of piezoresistive sense die in close proximity to one another further comprises:

placing each of said plurality of piezoresistive sense die between a conductive seal stack; and locating said conductive seal stack on a PCB held captive by a housing.

12. An apparatus for monitoring manual patient injections through an intravenous line, comprising:

a plurality of piezoresistive sense die configured in close proximity to one another, wherein said plurality of piezoresistive sense die is in intimate contact with a flow diaphragm on either side of an orifice formed in the intravenous line;

a plurality of plungers associated with said plurality of piezoresistive sense die, wherein a force from said flow diaphragm is transferred to said plurality of piezoresistive sense die through a plurality of plungers that make intimate contact with said flow diaphragm on either side of said orifice; and at least one electrical component for performing a signal compensation, wherein said at least one electrical component is associated with said plurality of piezoresistive sense die to thereby provide a thermal calibration and a differential calculation, such that said at least one electrical component is configured to communicate electronically with external electronics to automatically monitoring manual patient injections through the intravenous line.

13. The apparatus of claim 12 wherein said plurality of piezoresistive sense die include at least two piezoresistive sense die and said plurality of plungers include at least two plungers.

14. The apparatus of claim 12 wherein:

each of said plurality of piezoresistive sense die is placed between a conductive seal stack; and said conductive seal stack is on a PCB held captive by a housing.

15. The apparatus of claim 14 wherein said conductive seal stack comprises at least one of the following: an environmental seal and a conductive seal.

16. The apparatus of claim 12 wherein:
each piezoresistive sense die among said plurality of piezoresistive sense die is fixed glued to a PCB;
a housing is located over said plurality of piezoresistive sense die; and
an orifice is formed above said plurality of piezoresistive sense die, wherein a gel is dispensed into said orifice, in order to make intimate contact with a top side of at least one piezoresistive sense die among said plurality of piezoresistive sense die.

17. The apparatus of claim 16 wherein said plurality of plungers and said flow diaphragm associated with said plurality of piezoresistive sense die is placed on top of said gel such that a force from said flow diaphragm is capable of being transmitted through said plurality of plungers and into said gel and finally into said plurality of piezoresistive sense die.

18. The apparatus of claim 12 further comprising:
a carrier, wherein each piezoresistive sense die among said plurality of piezoresistive sense die is glued to said carrier;
an orifice formed in said carrier, wherein a gel is dispensed into said orifice in order to allow said gel to make intimate contact with an etched side of said at least one piezoresistive sense die among said plurality of piezoresistive sense die, such that said flow diaphragm is placed over said gel; and
a cover located over said carrier to maintain said flow diaphragm in place and to provide an environmental seal.

19. The apparatus of claim 18 wherein said carrier is fixed to a PCB so that said at least two piezoresistive sense die are electrically connected to one another.

* * * * *